US00PP29079P2

(12) United States Plant Patent
Holtmaat

(10) Patent No.: US PP29,079 P2
(45) Date of Patent: Mar. 6, 2018

(54) ***MONARDA* PLANT NAMED 'MON0005BTR'**

(50) Latin Name: *Monarda didyma*
Varietal Denomination: MON0005BTR

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/330,933

(22) Filed: Nov. 15, 2016

(51) Int. Cl.
*A01H 5/02* (2006.01)

(52) U.S. Cl.
USPC ..... Plt./455

(58) Field of Classification Search
USPC ..... Plt./455
See application file for complete search history.

(56) References Cited

PUBLICATIONS

UPOV hit on *Monarda* plant named 'MON0005BTR', QZ PBR 20162316; filed Sep. 23, 2016.*

* cited by examiner

*Primary Examiner* — Anne M Grunberg
(74) *Attorney, Agent, or Firm* — C. A. Whealy

(57) ABSTRACT

A new and distinct cultivar of *Monarda* plant named 'MON0005BTR', characterized by its broadly upright plant habit; dark green-colored leaves; freely flowering habit; large inflorescences with purple-colored flowers; long flowering period; and tolerance to Powdery Mildew.

2 Drawing Sheets

Botanical designation: *Monarda didyma.*
Cultivar denomination: 'MON0005BTR'.

BACKGROUND OF THE INVENTION

The present invention relates to a new and distinct cultivar of *Monarda* plant, botanically known as *Monarda didyma*, typically grown a container plant and hereinafter referred to by the name 'MON0005BTR'.

The new *Monarda* plant is a product of a planned breeding program conducted by the Inventor in Zuidwolde, The Netherlands. The objective of the breeding program is to create new *Monarda* plants with attractive flowers and tolerance to Powdery Mildew.

The new *Monarda* plant originated from an open-pollination during the summer of 2013 of an unnamed selection of *Monarda didyma*, not patented, as the female, or seed, parent with an unknown selection of *Monarda didyma*, as the male, or pollen, parent. The new *Monarda* plant was discovered and selected by the Inventor as a single flowering plant from within the progeny of the stated open-pollination grown in a controlled nursery environment in Zuidwolde, The Netherlands during the summer of 2014.

Asexual reproduction of the new *Monarda* plant by cuttings in Zuidwolde, The Netherlands, since June, 2016 has shown that the unique features of this new *Monarda* plant are stable and reproduced true to type in successive generations.

SUMMARY OF THE INVENTION

Plants of the new *Monarda* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MON0005BTR'. These characteristics in combination distinguish 'MON0005BTR' as a new and distinct *Monarda* plant:

1. Broadly upright plant habit.
2. Dark green-colored leaves.
3. Freely flowering habit.
4. Large inflorescences with purple-colored flowers.
5. Long flowering period.
6. Tolerant to Powdery Mildew.

Plants of the new *Monarda* differ primarily from plants of the female parent selection in plant uniformity as plants of the new *Monarda* are more uniform than plants of the female parent selection.

Plants of the new *Monarda* can be compared to plants of *Monarda didyma*×*Monarda fistulosa mentaefolia* 'Petite Delight', disclosed in U.S. Plant Pat. No. 10,784. In side-by-side comparisons, plants of the new *Monarda* differ from plants of 'Petite Delight' in the following characteristics:

1. Plants of the new *Monarda* are more freely flowering and have larger flowers than plants of 'Petite Delight'.
2. Plants of the new *Monarda* flower for a longer period of time than plants of 'Petite Delight'.
3. Flowers of plants of the new *Monarda* are not persistent whereas flowers of plants of 'Petite Delight' are persistent.
4. Plants of the new *Monarda* are more tolerant to Powdery Mildew than plants of 'Petite Delight'.

BRIEF DESCRIPTION OF THE PHOTOGRAPHS

The accompanying colored photographs illustrate the overall appearance of the new *Monarda* plant showing the colors as true as it is reasonably possible to obtain in colored reproductions of this type. Colors in the photographs may differ slightly from the color values cited in the detailed botanical description which accurately describe the actual colors of the new *Monarda* plant.

The photograph on the first sheet is a side perspective view of a typical flowering plant of 'MON0005BTR' grown in a container.

The photograph at the top of the second sheet is a close-up view of the upper surface of typical leaves of 'MON0005BTR'.

The photograph at the bottom of the second sheet is a close-up view of a typical inflorescence of 'MON0005BTR'.

DETAILED BOTANICAL DESCRIPTION

The aforementioned photographs and following observations, measurements and values describe plants grown during the late spring in 21-cm containers in a polyethylene-covered structure in Zuidwolde, The Netherlands and under cultural practices typical of commercial *Monarda* production. During the production of the plants, day temperatures ranged from 12° C. to 25° C. and night temperatures ranged from 4° C. to 15° C. Plants were two years old when the photographs and the description were taken. In the detailed description, color references are made to The Royal Horticultural Society Colour Chart, 2007 Edition, except where general terms of ordinary dictionary significance are used.

Botanical classification: *Monarda didyma* 'MON0005BTR'.

Parentage:

*Female, or seed, parent*.—Unnamed selection of *Monarda didyma*, not patented.

*Male, or pollen, parent*.—Unknown selection of *Monarda didyma*, not patented.

Propagation:

*Type cutting*.—By cuttings.

*Time to initiate roots, summer*.—About two weeks at temperatures about 20° C.

*Time to produce a rooted young plant, summer*.—About two months at temperatures about 20° C.

*Root description*.—Medium in thickness, fibrous; typically creamy white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial; broadly upright plant form; overall plant form, inverted triangle; moderately vigorous growth habit.

*Plant height*.—About 62 cm.

*Plant width*.—About 56.5 cm.

*Lateral branch description*.—Branching habit: Freely basal branching habit with about five main stems, each main stem with lateral branches. Length: About 17 cm. Diameter: About 3 mm. Internode length: About 6.8 cm. Strength: Strong. Aspect: Mostly upright. Texture and luster: Moderately pubescent; slightly glossy. Color: Close to 144A.

Leaf description:

*Arrangement*.—Opposite, simple.

*Length*.—About 11.9 cm.

*Width*.—About 8.4 cm.

*Shape*.—Ovate.

*Apex*.—Acuminate.

*Base*.—Truncate to cordate.

*Margin*.—Serrate.

*Texture and luster, upper surface*.—Densely pubescent and moderately rugose; slightly glossy.

*Texture and luster, lower surface*.—Densely pubescent; matte.

*Venation pattern*.—Pinnate.

*Fragrance*.—Moderately fragrant; pleasant, spicy.

*Color*.—Developing leaves, upper surface: Close to 143A. Developing leaves, lower surface: Close to 143C. Fully expanded leaves, upper surface: Darker than between N137A and 147A; venation, close to 144A. Fully expanded leaves, lower surface: Close to 137A to 137B; venation, close to 144B to 144C.

*Petioles*.—Length: About 1.8 cm. Diameter: About 3 mm by 3.5 mm. Color, upper and lower surfaces: Close to 144B; proximally, occasionally tinged with close to 182B.

Flower description:

*Flower form, arrangement and flowering habit*.—Single labiate flowers arranged in large terminal globular spikes; flowers face outwardly; freely flowering habit with about 200 flowers developing per inflorescence and about 1,000 flowers developing per plant during the flowering season.

*Natural flowering season*.—Long flowering habit, plants flower from mid-July to mid-September in The Netherlands.

*Postproduction longevity*.—Flowers maintain good substance for about five days on the plant; flowers not persistent.

*Fragrance*.—Faintly to moderately fragrant; pleasant, spicy.

*Flower buds*.—Length: About 1.9 cm. Diameter: About 3 mm. Shape: Narrowly oblanceolate; curved. Color: Close to 79B; proximally, close to N79C; immature calyx, close to 145C and 147A.

*Inflorescence height*.—About 4.8 cm.

*Inflorescence diameter*.—About 8.7 cm.

*Flower length (vertical)*.—About 1.9 cm.

*Flower diameter (horizontal)*.—About 8 mm.

*Flower depth (height)*.—About 3.9 cm.

*Petals*.—Arrangement: Labiate; upper lip hooded; lower lip, a single lobe; lips fused 60% of total length. Length, upper and lower lips: About 3.4 cm. Width, upper lip: About 4 mm. Width, lower lip: About 8 mm. Shape, upper lip: Lanceolate; apex, acute. Shape, lower lip: Oblanceolate; apex, caudate. Margin, upper and lower lips: Entire; lower petal, slightly undulate. Texture and luster, upper and lower lips, upper surface: Smooth, glabrous; matte. Texture and luster, upper and lower lips, lower surface: Moderately pubescent; matte. Color, upper and lower lips: When opening and fully opened, upper surface: Close to N79C; color becoming closer to N79B with development. When opening and fully opened, lower surface: Close to N79B to N79C; color becoming closer to N79B with development.

*Sepals*.—Quantity and arrangement: Five in a single whorl; lower 85% fused into a tubular calyx. Length: About 9 mm. Width: About 0.5 mm. Apex: Narrowly acute. Margin: Free parts, finely serrate. Texture and luster, upper and lower surfaces: Pubescent; dull.

Color: When opening, upper and lower surfaces: Close to 145C; free parts, close to 147A. Fully opened, upper and lower surfaces: Close to 145C; free parts, close to 147A.

*Pedicels*.—Length: About 1 mm. Diameter: About 0.5 mm. Strength: Moderately strong. Color: Close to 147C.

*Inflorescence bracts*.—Quantity and arrangement: About eleven at the base of inflorescence. Length: About 2 cm. Width: About 1.4 cm. Shape: Ovate to narrowly ovate; apex, acute. Margin: Entire. Texture, upper surface: Glabrous; velvety. Texture, lower surface: Pubescent. Color: When opening and fully opened, upper surface: Close to 145B and 145C heavily flushed and tinged with close to N186C. When opening and fully opened, lower surface: Close to 148A.

*Reproductive organs*.—Stamens: Quantity per flower: Two. Filament length: About 1.7 cm. Filament color: Close to N78C to N78D. Anther length: About 2 mm. Anther shape: Narrowly elliptic. Anther color: Close to N77D. Pollen amount: Scarce to moderate. Pollen color: Close to 4B. Pistils: Quantity per flower: One. Pistil length: About 3.3 cm. Stigma shape: Cleft, unequal. Stigma color: Close to 86B. Style length: About 3.1 cm. Style color: Close to 86B and 86C; towards the base, close to NN155C to NN155D. Ovary color: Close to 150B.

*Seed and fruit*.—Seed and fruit production have not been observed on plants of the new *Monarda*.

Pathogen & pest resistance: Plants of the new *Monarda* have been observed to be tolerant to Powdery Mildew (*Erysiphe cichoracearum*). Plants of the new *Monarda* not been observed to be resistant to pests and other pathogens common to *Monarda* plants.

Garden performance: Plants of the new *Monarda* have exhibited good tolerance to rain, wind and high temperatures about 30° C. and to be hardy to USDA Hardiness Zone 5.

It is claimed:

1. A new and distinct *Monarda* plant named 'MON0005BTR' as illustrated and described.

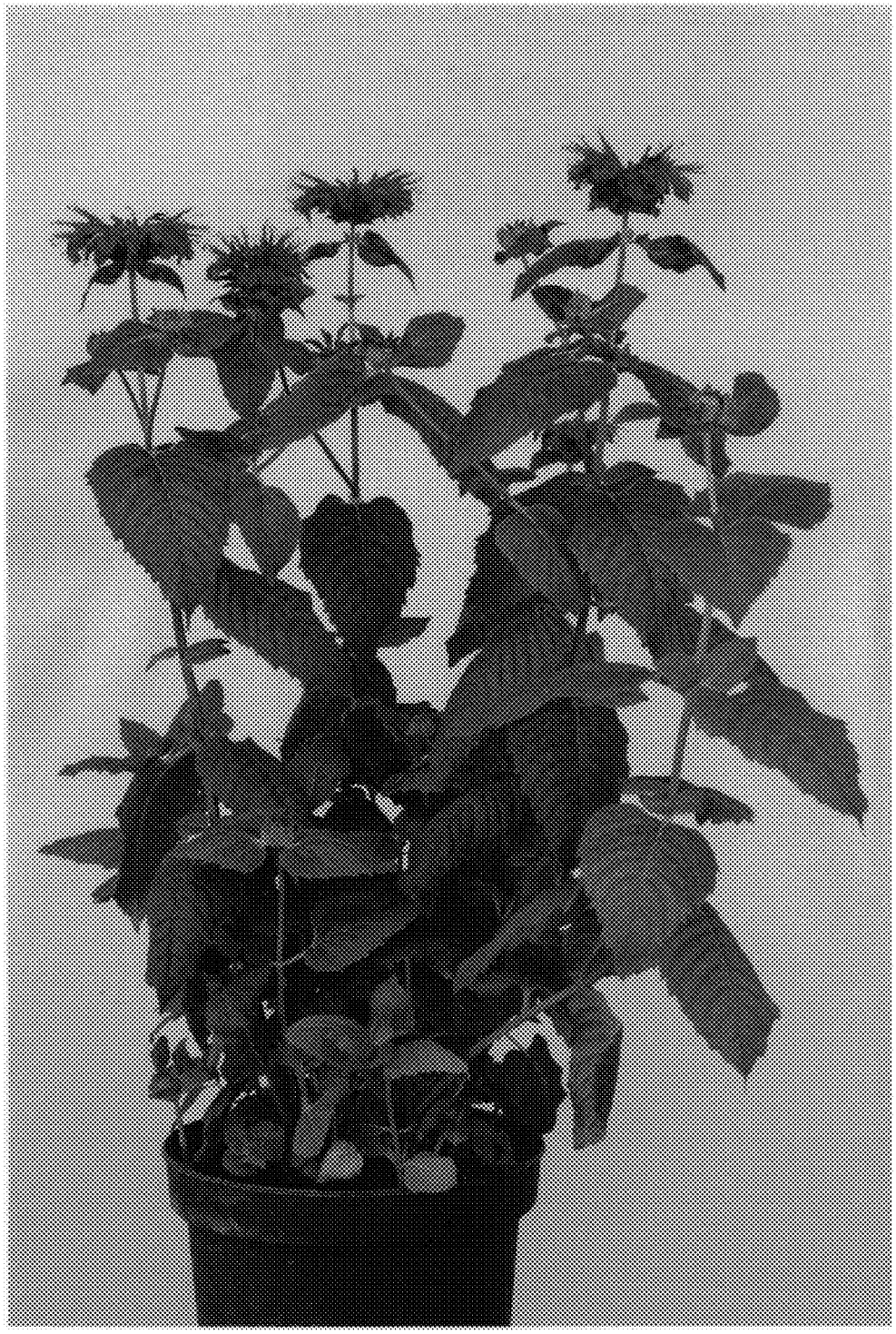

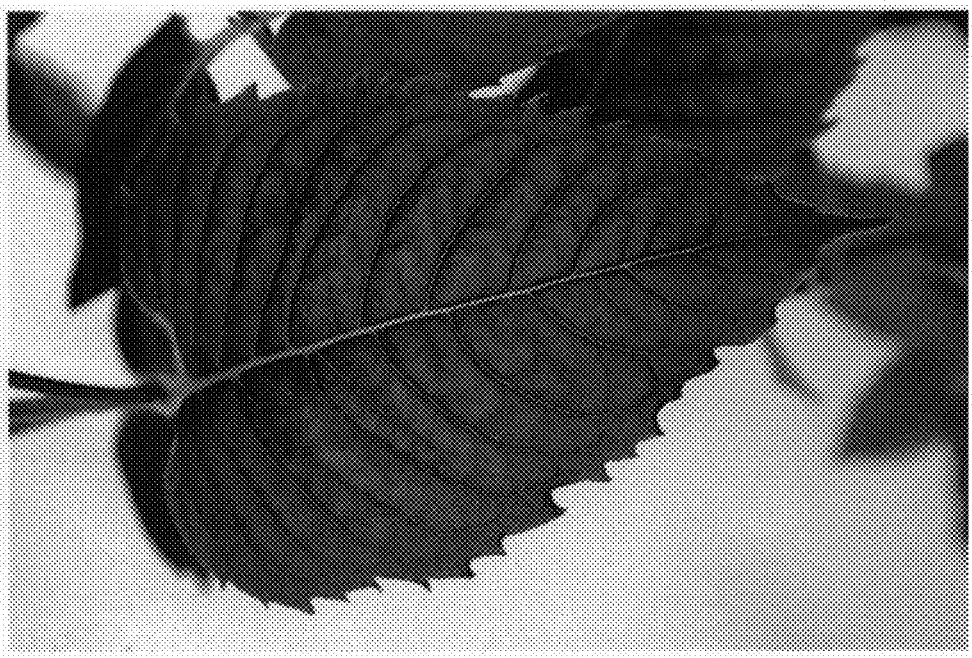
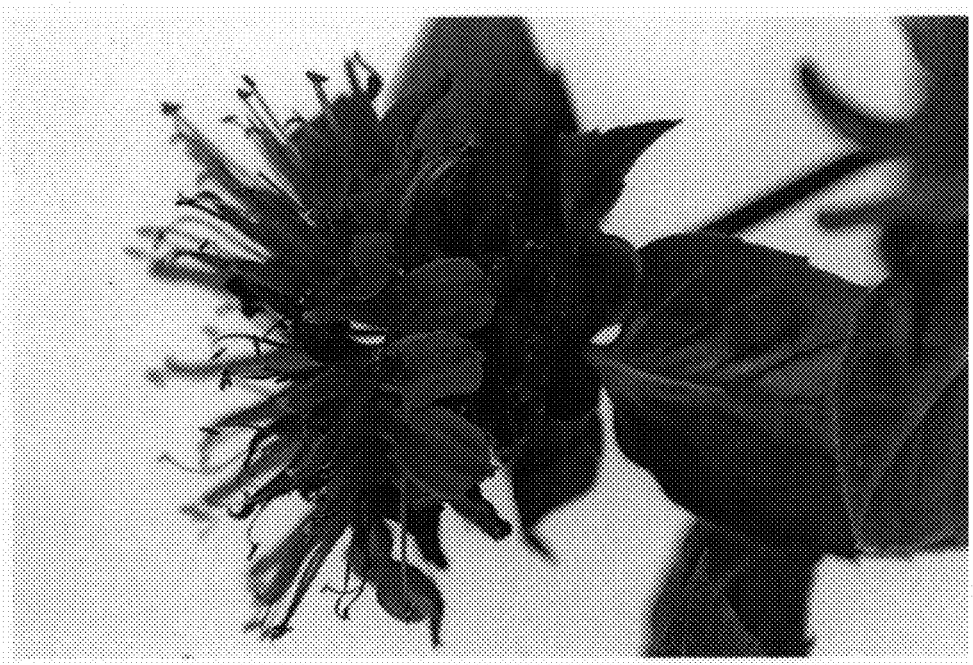

* * * * *